United States Patent [19]

Sogli et al.

[11] Patent Number: 5,043,483

[45] Date of Patent: Aug. 27, 1991

[54] PROCESS FOR THE ALKYLATION OF PHENOLS

[75] Inventors: Loris Sogli; Raffaele Ungarelli; L. Lawrence Chapoy, all of Novara, Italy

[73] Assignee: Montedison S.p.A., Milan, Italy

[21] Appl. No.: 276,634

[22] Filed: Nov. 28, 1988

[30] Foreign Application Priority Data

Dec. 1, 1987 [IT] Italy ................ 22821 A/87

[51] Int. Cl.$^5$ ............................................ C07C 39/12
[52] U.S. Cl. ........................ 568/744; 568/717; 568/718; 568/731; 568/734; 568/735
[58] Field of Search ............ 568/744, 734, 735, 763, 568/717, 718

[56] References Cited

U.S. PATENT DOCUMENTS 2,714,120  7/1955  Kehe .................................. 568/791
2,793,239  5/1957  Toland ............................... 568/794

FOREIGN PATENT DOCUMENTS

| 0319310 | 6/1989 | European Pat. Off. ............ 568/744 |
| 0347835 | 12/1989 | European Pat. Off. ............ 568/744 |
| 0188535 | 11/1982 | Japan ................................. 568/744 |
| 0140035 | 8/1983 | Japan ................................. 568/744 |
| 228694 | 2/1969 | U.S.S.R. ............................ 568/744 |
| 330151 | 4/1972 | U.S.S.R. ............................ 568/744 |
| 0929622 | 5/1982 | U.S.S.R. ............................ 568/744 |
| 8912037 | 12/1989 | World Int. Prop. O. . |
| WO8912037 | 12/1989 | World Int. Prop. O. .......... 568/744 |

*Primary Examiner*—Werren B. Lone
*Attorney, Agent, or Firm*—Stevens, Davis, Miller & Mosher

[57] ABSTRACT

Process for the alkylation of phenols comprising reacting a phenol with a vinyl-aromatic hydrocarbon in the presence of an acidic catalyst and of a solvent.

16 Claims, No Drawings

PROCESS FOR THE ALKYLATION OF PHENOLS

DESCRIPTION OF THE INVENTION

The present invention relates to a process for the alkylation of phenols. More particularly, this invention relates to a process for the alkylation of phenols with a high yield and selectivity to a mono-alkylated product.

The alkylation of phenols with olefins in the presence of acidic catalyst is a per se known process, although not widely used on a commercial scale owing to its low reaction yields.

For example, U.S. Pat. Nos. 2,932,806 and 2,722,556 disclose the alkylation of phenols with olefins in the presence of such acidic catalysts as sulphuric acid or phosphoric acid. However, according to these processes, very low yields of mono-alkylated product, even lower than 50%, or selectivities to di-alkylated products higher than 90% are obtained.

In Japanese patent applications Nos. 58/140,035 and 59/112,935, the above mentioned drawback purports to be partially overcome; in fact, these Japanese patent applications disclose the preparation of mono-alkyl-substituted hydroquinone by reaction of hydroquinone with vinyl-aromatic hydrocarbons, to obtain reaction yields of the order of 90-93%. However, these processes are not free from drawbacks, in that the alkylation, in order to achieve such highly satisfactory outcome, must be carried out either by using the same reaction product as the solvent, or by causing the reaction to take place in the presence of a poly-substituted hydroquinone.

U.S. Pat. No. 4,661,645 discloses the synthesis of (1-phenyl-ethyl)-hydroquinone from styrene and hydroquinone in the presence of a Lewis acid and in homogeneous phase, with an alkyl ether being used as the homogenizing solvent. In this case, too, the reaction product contains large amounts of di(phenyl-ethyl)hydroquinone, which may be higher than 30% by weight relative to the mixture of mono- and di-substituted products.

It has now been discovered (in accordance with the present invention) that the drawbacks of the prior art can be overcome by a process for the alkylation of phenols wherein the reaction takes place in heterogeneous phase.

Therefore, the object of the present invention is a process for the alkylation of phenols, comprising reacting a phenol with a vinyl-aromatic hydrocarbon in the presence of an organic solvent and of a catalyst comprising or consisting essentially of an inorganic acid diluted in water.

Examples of phenols which may be used in the process of the present invention are hydroquinone, resorcinol, pyrocatechol, pyrogallol, benzophenol, cresols, p-octyl-phenol, di-hydroxy-diphenyl, alpha-naphthol, beta-naphthol, and so forth. A particularly preferred reactant is hydroquinone.

The vinyl-aromatic hydrocarbon is preferably selected from those of the formula:

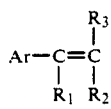
(I)

wherein:

Ar represents an aryl group containing from 6 to 18 carbon atoms, and $R_1, R_2$ and $R_3$, which may be the same as or different from one another, are selected from hydrogen or alkyl radicals of from 1 to 10 carbon atoms.

Examples of reactants of formula (I) are styrene, alpha-methyl-styrene, alpha-ethyl-styrene, p-methyl-styrene, p-isopropyl-styrene, p-methyl-alpha-methyl-styrene, beta-methyl-styrene, vinyl-naphthalene, and so forth. A particularly preferred reactant is styrene.

According to a preferred form of practical embodiment of the present invention, the phenol is employed in a slight molar excess with respect to the aromatic hydrocarbon. Molar ratios of phenol/vinyl-aromatic hydrocarbon within the range of from 1.5 to 1, and preferably within the range of from 1.3 to 1, are those used to the greatest advantage.

The alkylation reaction is carried out in a solvent having a boiling temperature compatible with the reaction temperature and a good solubility for both the reactants and the end products. Suitable solvents are the aromatic hydrocarbons, such as toluene, xylenes, and so forth.

The solvent may be used in any weight ratios relative to the phenol; however, weight ratios solvent/phenol within the range of from 0.5 to 5, and preferably within the range of from 1 to 2, are preferred.

Any inorganic acid can be used as the catalyst of the alkylation process according to the present invention, although ortho-phosphoric acid, pyro-phosphoric acid, and sulphuric acid, diluted in water at 60-90%, and preferably at 70-80% by weight of the acid, are preferred.

The catalyst is used in molar ratios relative to the phenol that are within the range of from 0.5 to 6, and preferably from 1 to 3.

The alkylation reaction is carried out under room pressure and at a temperature within the range of from 90° to 120° C., and preferably of from 110° to 115° C.

At the end of the alkylation reaction the organic phase constituted by the solvent and by the raw reaction product is decanted off from the catalytic system, and the solvent is then evaporated off.

According to the process of the present invention, a yield of mono-alkylated product higher than 95% and a selectivity with respect to di-alkylated product lower than 5% may be obtained, with a purity referred to mono- and di-alkylated products higher than 99.9%.

In the alkylation of hydroquinone, the process according to the present invention is particularly interesting in that it makes it possible for the raw reaction product to be used for producing polymers, in particular for producing thermotropic liquid-crystalline aromatic polyesters, without further purification which would have a considerable effect on both the yield and the costs. In fact, mono-alkylated hydroquinone is a glass-like, non-crystallizable solid which can only be purified by distillation, during which the product is subject to thermal breakdown due to the required operating conditions, e.g., at temperatures higher than 180° C. and operating pressures lower than 1 mbar.

In order still better to understand the present invention and to practice it, some illustrative but non-limitative examples are reported below.

EXAMPLE 1

To a glass reactor of 250 ml fitted with stirrer, thermometer, reflux condenser, dripping funnel, and external heating bath, 26.4 g (0.24 mol) of hydroquinone, 50 ml of xylene, and 110 g of H$_3$PO$_4$ as an aqueous solution at 75% by weight, were charged.

The reaction mixture was heated to 113° C. and styrene was added in an amount of 20.8 g (0.2 mol). After a 3-hour stirring at 115°–116° C., the two phases were allowed to separate; the solution of H$_3$PO$_4$ was removed; and the xylenic solution was washed with NaHCO$_3$, using an aqueous solution at 5% by weight, and water.

After evaporating xylene, 41.4 g of a uniform glass-like product was obtained, with a gas-chromatographic titer of 96% of (1-phenyl-ethyl)-hydroquinone and 3.9% of di(phenyl-ethyl)hydroquinone, equivalent to a molar yield of (1-phenylethyl)hydroquinone/styrene of 95.9%.

EXAMPLES 2–8

The process is carried out as in Example 1, but with such amounts, and under such operating conditions, and with such results as are reported below in Table 1:

TABLE 1

| Example No. | Hydroquinone g | Sytrene g | H$_3$PO$_4$ 75% sol. g | Xylene ml | Temp. °C. | Time hours | Product g | SHQ % | DSHQ % | SHQ styrene molar yield, % |
|---|---|---|---|---|---|---|---|---|---|---|
| 2 | 24.2 | 18.3 | 144 | 100 | 105 | 5 | 37.2 | 97 | 2.9 | 95.8 |
| 3 | 26.4 | 20.3 | 131 | 50 | 115 | 2.5 | 41.3 | 96.5 | 3.4 | 95.4 |
| 4 | 22 | 19.7 | 26 | 25 | 115 | 3 | 40.1 | 97 | 2.9 | 96.0 |
| 5 | 22 | 16.2 | 52 | 50 | 113 | 3 | 33 | 97 | 2.9 | 96.0 |
| 6 | 28.6 | 20.8 | 98 | 50 | 115 | 2.5 | 42.5 | 97 | 2.9 | 96.2 |
| 7 | 28.6 | 20.8 | 131 | 75 | 115 | 4 | 42.6 | 98 | 1.9 | 97.5 |
| 8 | 22 | 16.7 | 26 | 50 | 110 | 3 | 34.0 | 98 | 1.9 | 97.2 |

NOTE:
SHQ = (1-phenylethyl)-hydroquinone
DSHQ = di(phenylethyl)hydroquinone

What is claimed is:

1. Process for the aralkylation of phenols, comprising reacting a phenol selected from the class consisting of hydroquinone, resorcinol, pyrocatechol, pyrogallol, benzophenol, cresols, p-octyl-phenol, di-hydroxydiphenyl, alpha-naphthol and beta-naphthol, with a vinyl aromatic hydrocarbon of the formula

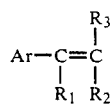

wherein:
Ar represents an aryl group containing from 6 to 18 carbon atoms, and
R$_1$, R$_2$ and R$_3$, which may be either equal or different from one another, are selected from the class consisting of hydrogen or alkyl radicals of from 1 to 10 carbon atoms,
in the presence of an organic solvent selected from the class consisting of toluene, xylenes and mixtures thereof and in the presence of a catalyst consisting essentially of an inorganic acid selected from the class consisting of ortho-phosphoric acid, pyrophosphoric acid and sulphuric acid diluted in water at 69–90% by weight.

2. Process according to claim 1, wherein the phenol is hydroquinone.

3. Process according to claim 1, wherein the vinyl-aromatic reactants are selected from the class consisting of styrene, alpha-methyl-styrene, alpha-ethyl-styrene, p-methyl-styrene, p-isopropyl-styrene, p-methyl-alpha-methyl-styrene, beta-methyl-styrene, and vinyl-naphthalene.

4. Process according to claim 1, wherein the vinyl-aromatic hydrocarbon is styrene.

5. Process according to claim 1, wherein the molar ratio of phenol/vinyl-aromatic hydrocarbon is within the range of from 1.5 to 1.

6. Process according to claim 1, wherein the weight ratio of the solvent to the phenol is within the range of from 0.5 to 5.

7. Process according to claim 1, wherein the catalyst is ortho-phosphoric acid, pyrophosphoric acid or sulphuric acid diluted in water at 60–90%.

8. Process according to claim 1, wherein the molar ratio of the catalyst to the phenol is within the range of from 0.5 to 6.

9. Process according to claim 1, wherein the reaction temperature is within the range of from 90° to 120° C.

10. Process according to claim 1, wherein the phenol is hydroquinone, and the vinyl-aromatic hydrocarbon is styrene.

11. Process according to claim 1, wherein the molar ratio of phenol/vinyl-aromatic hydrocarbon is within the range of from 1.3 to 1.

12. Process according to claim 1, wherein the weight ratio of the solvent to the phenol is within the range of from 1 to 2.

13. Process according to claim 1, wherein the catalyst is ortho-phosphoric acid, pyrophosphoric acid or sulphuric acid diluted in water at 70–80% by weight.

14. Process according to claim 1, wherein the molar ratio of the catalyst to the phenol is within the range of from 1 to 3.

15. Process according to claim 1, wherein the reaction temperature is within the range of from 110° to 115° C.

16. Process according to claim 1, wherein the molar ratio of phenol/vinyl-aromatic hydrocarbon is within the range of about 1.06 to about 1.3.

* * * * *